US010307759B2

United States Patent
Immink et al.

(10) Patent No.: US 10,307,759 B2
(45) Date of Patent: Jun. 4, 2019

(54) BIOSENSOR FOR THE DETECTION OF TARGET COMPONENTS IN A SAMPLE

(71) Applicant: KONINKLIJKE PHILIPS N.V., Eindhoven (NL)

(72) Inventors: Albert Hendrik Jan Immink, Eindhoven (NL); Jeroen Hans Nieuwenhuis, Eindhoven (NL); Gwenola Sabatte, Eindhoven (NL); Wilhelmina Maria Hardeman, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 9 days.

(21) Appl. No.: 15/319,068

(22) PCT Filed: Jun. 24, 2015

(86) PCT No.: PCT/EP2015/064188
§ 371 (c)(1),
(2) Date: Dec. 15, 2016

(87) PCT Pub. No.: WO2015/197659
PCT Pub. Date: Dec. 30, 2015

(65) Prior Publication Data
US 2017/0113223 A1   Apr. 27, 2017

(30) Foreign Application Priority Data

Jun. 25, 2014   (EP) .................................... 14173795

(51) Int. Cl.
*B01L 3/00* (2006.01)
*G01N 33/543* (2006.01)

(52) U.S. Cl.
CPC ... *B01L 3/502761* (2013.01); *B01L 3/502738* (2013.01); *B01L 3/502784* (2013.01);
(Continued)

(58) Field of Classification Search
CPC ....... B01L 3/502761; G01N 33/54393; C12M 1/00
See application file for complete search history.

(56) References Cited

U.S. PATENT DOCUMENTS

| 6,605,454 B2 * | 8/2003 | Barenburg | ............. | C12N 1/066 219/690 |
| 2011/0065211 A1 * | 3/2011 | Nieuwenhuis | ....... | G01N 27/745 436/501 |

(Continued)

FOREIGN PATENT DOCUMENTS

| EP | 2128617 A1 | 12/2009 |
| WO | 2008115723 A1 | 9/2008 |

(Continued)

OTHER PUBLICATIONS

Gottheil, Raiah et al "Moving the Solid Phase: A Stationary Microfluidics Platform Technology for Cartridge Based Sandwich Immunoassays", 17th International Conference on Miniaturized Systems for Chemistry and Life Sciences, Oct. 2013.

(Continued)

*Primary Examiner* — Narayan K Bhat

(57) ABSTRACT

The invention relates to a method and a biosensor system (300) for the detection of target components (TC) in a biological sample. In a preferred embodiment, magnetic purification particles (PP) are added to the sample that can bind interfering components (IC) (if present) which interfere with the detection process. The purification particles (PP) with bound interfering components (IC) may be removed from the sample and transferred through a magneto-capillary valve (MCV1) into a waste chamber (320).

14 Claims, 4 Drawing Sheets

(52) U.S. Cl.
CPC . *G01N 33/54326* (2013.01); *G01N 33/54393* (2013.01); *B01L 2200/0647* (2013.01); *B01L 2200/0668* (2013.01); *B01L 2200/0673* (2013.01); *B01L 2200/141* (2013.01); *B01L 2300/087* (2013.01); *B01L 2300/0816* (2013.01); *B01L 2400/043* (2013.01); *B01L 2400/0688* (2013.01)

(56) References Cited

U.S. PATENT DOCUMENTS

| | | | |
|---|---|---|---|
| 2012/0270332 A1 | 10/2012 | Wimberger-Friedl | |
| 2013/0034845 A1 | 2/2013 | Kelso | |
| 2013/0156643 A1 | 6/2013 | Rodenfels | |
| 2013/0302787 A1 | 11/2013 | Agarwal | |

FOREIGN PATENT DOCUMENTS

| | | | |
|---|---|---|---|
| WO | 2009083862 A1 | 7/2009 | |
| WO | 2009125339 A2 | 10/2009 | |
| WO | 2010041174 A1 | 4/2010 | |
| WO | 2010070461 A1 | 6/2010 | |
| WO | 2010140128 A1 | 12/2010 | |
| WO | 2011007310 A1 | 1/2011 | |
| WO | 2011036634 A1 | 3/2011 | |
| WO | 2011042828 A1 | 4/2011 | |
| WO | 2014001985 A1 | 1/2014 | |

OTHER PUBLICATIONS

Mauk, Michael G. et al "Lab-on-a-Chip Technologies for Oral-Based Cancer Screening and Diagnostics", Ann. N.Y. Acad. Sei. vol. 1098: pp. 467-475, 2007.

Den Dulk, Remco C. "Magneto-capillary valve for integrated purification and enrichment of nucleic acids and proteins", Lab on a Chip vol. 13, No. 106, 2013.

Wang, Jingjing et al , "Microfluidic platform for isolating nucleic acid targets using sequence specific hybridization", Biomicrofluidics, vol. 7, 2013.

Den Dulk, Remco C., "Magneto-capillary valve for integrated biological sample preparation", Technische University Eindhoven, 2011.

Van Reenen, Alexander et al "Integrated lab-on-chip biosensing systems based on magnetic particle actuation—a comprehensive review", Lab on a Chip 2014.

* cited by examiner

BIOSENSOR FOR THE DETECTION OF TARGET COMPONENTS IN A SAMPLE

CROSS-REFERENCE TO PRIOR APPLICATIONS

This application is the U.S. National Phase application under 35 U.S.C. § 371 of International Application No. PCT/EP2015/064188, filed on Jun. 24, 2015, which claims the benefit of European Patent Application No. 14173795.7, filed on Jun. 25, 2014. These applications are hereby incorporated by reference herein.

FIELD OF THE INVENTION

The invention relates to a method and a biosensor system for the detection of target components in a biological sample.

BACKGROUND OF THE INVENTION

A microfluidic device has been described in literature that comprises a magneto-capillary valve (Remco C. den Dulk, Kristiane A. Schmidt, Gwénola Sabatté, Susana Liébana, Menno W. J. Prins: "Magneto-capillary valve for integrated purification and enrichment of nucleic acids and proteins", Lab Chip, 2013, 13, 106). In said device, target components such as nucleic acids and proteins are bound to magnetic beads which are then transferred into a neighboring chamber through a magneto-capillary valve.

SUMMARY OF THE INVENTION

Based on this background, it was an object of the present invention to provide means that allow for an alternative and preferably more robust detection of target components in a sample.

This object is addressed by a biosensor system according to claim 1 and a method according to claim 2. Preferred embodiments are disclosed in the dependent claims.

According to a first aspect, an embodiment of the invention relates to a biosensor system for the detection of target components in a sample, wherein said sample may possibly comprise interfering components which may interfere with the detection of the target components. The sample will typically be a fluid of biological origin, for example a droplet of blood, saliva or urine. The "target components" will typically be biological molecules of interest such as nucleic acids or proteins. Similarly, the "interfering components" will typically be molecules that are occasionally or always present in a respective sample, wherein they may be of natural origin (e.g. body substances) or artificial origin (e.g. contaminants). The biosensor system comprises the following components:

- A first chamber which is called "purification chamber" in the following and which comprises an inlet for the introduction of the sample.
- A second chamber which is called "waste chamber" in the following and which is connected to the aforementioned purification chamber by a (first) magneto-capillary valve.
- First particles that will be called "purification particles" in the following and that can bind interfering components (if present) of the sample in the purification chamber.
- Second, magnetic particles that will be called "detection particles" in the following and that can bind target components (if present) of the sample.

The biosensor system is typically designed as a microfluidic device for the accommodation and processing of small amounts of fluids (sample and reagents), wherein said device typically comprises, additionally to the above mentioned components, further chambers, channels, inlets, outlets, valves, and/or pumping elements etc. The biosensor system may particularly be designed as a disposable cartridge intended for a single detection of target components in the biological sample.

The "purification particles" and the "detection particles" may comprise permanently magnetic particles and/or magnetizable particles, for example superparamagnetic beads. The size of these magnetic particles typically ranges between 3 nm and 50 µm.

The binding between purification particles and interfering components and/or between detection particles and target components may be a physical binding (e.g. by adhesion) or preferably a chemical binding (e.g. by hybridization or specific covalent binding).

The (first) "valve" is generally a connection between two chambers or compartments through which substances and particularly the purification particles (with or without bound interfering components) can controllably be moved. It is a "magneto-capillary valve", i.e. an element or component that is disposed between two chambers and through which magnetic particles can be moved by magnetic forces. A central area of this magneto-capillary valve is typically repellent for the fluids that are processed (e.g. hydrophobic if aqueous liquids are processed). Fluids of the adjacent chambers will therefore not cross the valve and mix, but magnetically responsive substances, e.g. magnetic beads, can actively be transferred through the valve by the application of magnetic forces. More details about "magneto-capillary valves" may for example be found in the WO2009083862, WO2010041174, WO2010070461, WO2010140128, WO2011007310, WO2011042828, in the article "Magneto-capillary valve for integrated purification and enrichment of nucleic acids and proteins" (above) and in the PhD. Thesis "Magneto-Capillary Valve for Integrated biological sample preparation" (R. C. den Dulk, ISBN: 978-90-286-2487-7, 2011).

According to a second aspect, an embodiment of the invention relates to a method for the detection of target components in a sample that possibly comprises interfering components which may interfere with the detection of the target components, said method comprising the following steps:

- Adding "purification particles", which can bind interfering components, to the sample.
- Transferring purification particles (with or without bound interfering components) from a purification chamber, in which they are accommodated together with the sample at hand, through a (first) magneto-capillary valve into a waste chamber.
- Adding magnetic "detection particles", which can bind target components, to the sample.
- Detecting detection particles that have bound to target components.

The biosensor system and the method are based on the same concept, i.e. the removal of interfering components from a sample by transferring them with the help of purification particles through a valve. Explanations and embodiments described for the biosensor system are therefore analogously valid for the method and vice versa.

The biosensor system and the method have the advantage that they allow for the detection of target components in a biological sample with high accuracy, reliability, and robustness. This is because interfering components that may possibly be present in the sample are securely removed through a valve after binding them to purification particles.

In the following, various preferred embodiments will be described which can be realized both with the biosensor system and the method (even if they are explained in detail only for one of them).

The types of interfering components that may occur and/or be relevant in a sample depend on the origin of said sample, on preprocessing steps, and on the assay that is intended for the detection of target components. In a preferred embodiment, the purification particles are adapted to bind at least one of the following interfering components (and/or fractions and/or aggregates thereof): proteins and/or fractions and/or aggregates thereof (e.g. glycoproteins, albumins, IgG, IgM, C1Q, fibrin, peptides), in particular antibodies, such as human anti-species antibodies (e.g. HAMA); lipids (e.g. triglycerids); nucleic acids and/or fragments and/or aggregates thereof (e.g. DNA, RNA, aptamers); cells (e.g. blood cells) and/or fractions thereof (e.g. hemoglobin); bacteria; enzymes (e.g. proteases); molecules with a certain resemblance to the target analytes that may cross-react; drugs; and other components that may interfere with an immunoassay.

In a simple case, the purification particles may be beads without a particular surface coating or the like for a specific binding of interfering components. Experiments show that even such unspecific purification particles may already improve detection results due to some nonspecific binding of interfering components. Most preferably, the purification particles may however comprise at least one of the following surface molecules or atoms (and/or fractions and/or aggregates thereof) to which interfering components can bind or with which they can react in another way: proteins and/or fractions and/or aggregates thereof, in particular streptavidin and/or antibodies that bind specifically to interfering components; nucleic acids and/or fragments and/or aggregates thereof (e.g. DNA, RNA, aptamers); enzymes (e.g. proteases); electrically charged molecules or atoms to bind unspecifically to oppositely charged interfering components; silica molecules; metal atoms such as gold atoms; molecules that may react with interfering factors to modify their properties such that the degree of interference is decreased; molecules with a certain resemblance to the target analytes; capture molecules with an affinity for components that may interfere with an immunoassay.

The purification particles may already be added to the sample and mixed with it prior to the introduction of the sample into the purification chamber.

Additionally or alternatively, at least a part of the purification particles (preferably all of them) may be provided in the purification chamber prior to the introduction of the sample into said chamber or may be provided in an additional chamber, called "purification-particle storage chamber", prior to the introduction of the sample into the purification chamber. The purification particles may for example be stored there in dried form until they are used.

The aforementioned purification-particle storage chamber may preferably be coupled to the purification chamber via a (second) valve, particularly a (second) magneto-capillary valve. This allows for a controlled transfer of purification particles into the purification chamber when they are required there (typically after introduction of the sample). In case of magneto-capillary valves and magnetic purification particles, the same magnetic field generator (e.g. a movable permanent magnet) can optionally be used for moving purification particles from their storage chamber into the purification chamber and thereafter (with bound interfering components) from the purification chamber into the waste chamber.

In another embodiment of the invention, the magnetic detection particles are added to the sample and mixed with it prior to its introduction into the purification chamber.

Additionally or alternatively, at least some of the magnetic detection particles (preferably all of them) may be provided in the purification chamber prior to the introduction of the sample into the purification chamber, or they may be provided in a separate chamber, called "detection-particle storage chamber", prior to the introduction of the sample into the purification chamber. The detection particles may for example be stored in dried form in the purification or the storage chamber.

The aforementioned detection-particle storage chamber is preferably coupled to the purification chamber via a (third) magneto-capillary valve. Again, one and the same magnetic device may optionally be used for the movement of magnetic purification particles and magnetic detection particles through the respective magneto-capillary valves.

The purification particles may particularly be particles that can actively be moved under the control of a user or of an apparatus. The purification particles may for example be particles that can be moved by magnetic, electrical, acoustic, thermal and/or optical effects or means, wherein such means are preferably comprised by the biosensor system.

The aforementioned "acoustic means" may particularly comprise a sound generator, for example an ultrasonic transducer with which a standing wave can be generated in the medium comprising the purification particles.

The above mentioned "thermal means" may particularly comprise a heater and/or a cooler with which local temperature differences can be generated in the medium comprising the purification particles.

The above mentioned "optical means" may particularly comprise a light source such as a laser or an LED with which spots in the medium that comprises the purification particles can be illuminated.

The purification particles may particularly comprise magnetic particles such as magnetizable beads. Magnetic purification particles can controllably be moved by magnetic means, for example by a magnetic field generator such as a permanent magnet.

Additionally or alternatively, the purification particles may comprise electrically interacting particles, for example ions and/or particles with an electrical polarization (e.g. dipoles). Such electrically interacting purification particles can controllably be moved by electrical forces or means, e.g. an electrical field generator such as a charged electrode and/or according to the principles of dielectrophoresis.

In a further embodiment of the invention, at least one "binding spot" is provided at an inner surface of the purification chamber and/or an inner surface of a separate "detection chamber", wherein magnetic detection particles with bound target components can bind at said binding spot (typically to binding sites or molecules that constitute the spot). Surface specific detection procedures can then be applied for the detection of said bound detection particles (thus allowing for the implicit detection of the attached target components). Examples of such procedures are Frustrated Total Internal Reflection (disclosed e.g. in the WO 2008/115723 A1, which is incorporated into the present text by reference), or the "double refraction detection" with e.g. a wedge-like optical structure at the binding spot (cf. e.g. WO 2009/125339 A2, which is incorporated into the present text by reference). Other examples comprise the optical detection of single beads (cf. e.g. WO 2011/036634A1, which is incorporated into the present text by reference).

According to another embodiment, the biosensor system comprises a "detection chamber" that is coupled to the purification chamber via a (fourth) magneto-capillary valve that allows for the transfer of magnetic detection particles from the purification chamber to said detection chamber. Thus an additional purification step can be implemented, i.e. the transfer of target components bound to detection particles into the detection chamber, where a clean matrix fluid can be provided for the uptake of the detection particles.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Figure 1:
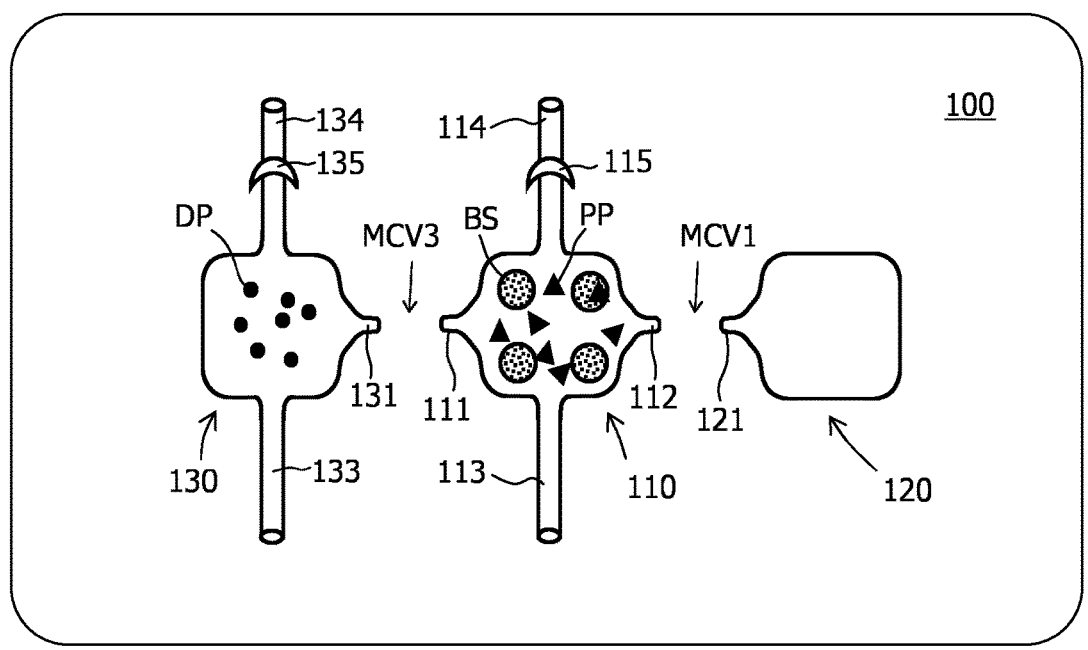
FIG. 1 schematically illustrates an embodiment of a biosensor system with a purification chamber, a waste chamber, and a detection-particle storage chamber prior to a purification and detection procedure.

The approach of the present invention can for example be applied in general biosensor assays with magnetic particles which can be manipulated by magnetic forces. In the following, certain embodiments of the invention will be illustrated with respect to exemplary biosensor technologies such as the Magnotech® biosensor technology developed by the applicant. In one application of this technology, measurements are done in whole blood. This blood is filtered to obtain plasma that fills a disposable cartridge by capillary action. Magnetic nanoparticles are integrated in a dried form in the cartridge. When the sample fluid enters the reaction chambers the dried beads start to dissolve again in the fluid.

When measuring blood samples of a large number of patients, most of them correlate well with an independent reference system. However, some samples may show deviating behavior. The results are either significantly higher or lower than one would expect based on the reference result. Based on their investigations, the inventors of the present invention suppose that several mechanisms can be the root-cause for these unexpected results:

- Clustering of the magnetic nanoparticles due to interfering components in the blood sample. Typically this results in a much lower signal.
- Some components in the blood sample may interfere with the incubation reaction.
- Some components in the blood sample may interfere with the binding reaction (e.g. human anti-mouse antibodies (HAMA) bind the antibodies on the magnetic particle and the sensor surface together even when there is no target molecule present).

In all cases a solution would be the elimination of the interfering components in the different assay steps. This may be done by adding scavengers such as mouse-IgG. These however, may again have other effects in the assay (e.g. polyMAK and Rheumatoid factor show an interference leading to false positives). Another solution is therefore proposed here that comprises two directions:

A. Depletion of the sample from interfering components by using magnetic separation. In this approach, in a first step magnetic nanoparticles ("purification particles") of a first type are added to the sample fluid. These purification particles can be coated with a functionalized layer to capture any interfering components from the sample. In a second step these purification particles should be removed and replaced by the magnetic nanoparticles of a second type ("detection particles") that are needed for the actual target assay.

B. Displacement of the sample with a clean (buffer) fluid. In this approach, in a first step the magnetic nanoparticles of the second type (detection particles) that are needed for the actual target assay are added to the sample. Then some time is allowed for incubation, whereby the target analyte is captured by the magnetic nanoparticle (detection particle, e.g. Ab-coated). The detection particles are then transferred to a clean assay fluid that is present in a second assay chamber ("detection chamber") where the binding step is completed. In this case potential interference during the binding step is resolved (e.g. elimination of human anti-mouse (HAMA) interaction whereby the bead is a-specifically coupled to the sensor surface via the mouse-based target antibodies).

Experiments according to approach A) show indeed that adding (bare) magnetic beads to a sample prior to adding the sample to a cartridge improves clustering and correlation. Apparently, already bare beads capture interfering components that otherwise would induce clustering or assay interference.

FIG. 1 schematically shows a top view onto a biosensor system 100 or cartridge according to a first embodiment of the above general concepts. The biosensor system 100 comprises a substrate (typically a transparent material such as glass or plastic) in which the following microfluidic components are formed:

A "purification chamber" 110 in which a sample to be analyzed can be processed. In the shown for example, the purification chamber 110 comprises one or more binding spots BS on one of its inner surfaces. The binding spots BS comprise binding sites to which magnetic detection particles with bound target components can bind. Moreover, the purification chamber 110 is connected to an inlet 113 comprising a channel and an external orifice through which sample can be introduced. Similarly, it is connected to an outlet 114 comprising a channel with an external orifice, wherein a fluidic stop 115 is provided in the associated channel to prevent an undesired outflow of sample. Furthermore, magnetic purification particles PP are stored, preferably in dry form, in the purification chamber 110.

A "waste chamber" 120 that is located adjacent to the purification chamber 110. The waste chamber 120 comprises a protrusion 121 pointing toward a mirror symmetric protrusion 112 of the purification chamber 110, wherein said protrusions are connected via a hydrophobic channel section. Thus a (first) magneto-capillary valve MCV1 is constituted between the purification chamber 110 and the waste chamber 120.

A detection-particle storage chamber 130 in which magnetic detection particles DP can be provided. This chamber is connected to an inlet 133 and an outlet 134 with a fluidic stop 135. It can be filled through the inlet 133 with magnetic detection particles DP during manufacturing of the biosensor system and/or at the beginning of an assay. Furthermore, this storage chamber 130 comprises a protrusion 131 that points to a mirror symmetric protrusion 111 of the purification chamber 110. As explained above, another magneto-capillary valve MCV3 is thus formed between the detection-particle storage chamber 130 and the purification chamber 110. The Figure illustrates a first phase of a detection assay in which magnetic purification particles PP are stored in dried form in the purification chamber 110 and in which the detection-particle storage chamber 130 has been filled with magnetic detection particles DP.

Figure 2:
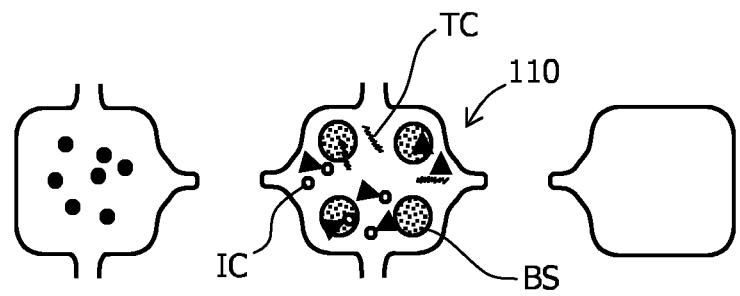
FIG. 2 illustrates the introduction of a sample into the purification chamber of the system of FIG. 1.

FIG. 2 illustrates the next step of the assay in which a biological sample comprising target components TC (e.g. nucleic acids) and (possibly) interfering components IC has been introduced into the purification chamber 110 through the inlet 113. During an incubation time, interfering components IC now bind to the magnetic purification particles PP.

Figure 3:
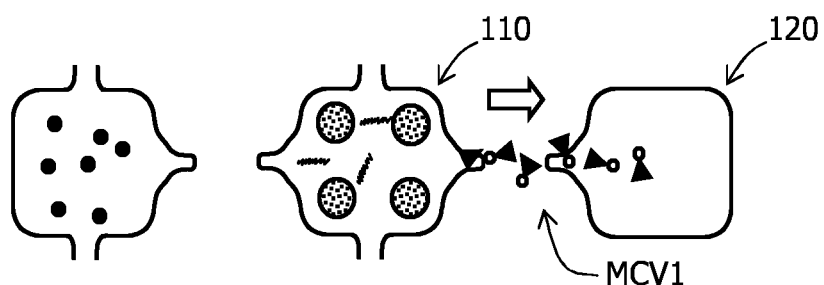
FIG. 3 illustrates the transfer of purification particles with bound interfering components into the waste chamber in the system of FIG. 1.

FIG. 3 illustrates a subsequent step of the assay in which magnetic purification particles PP (with or without bound interfering components IC) are actively transferred through the first magneto-capillary valve MCV1 into the waste chamber 120. The remaining sample is thus substantially freed of interfering components IC.

Figure 4:
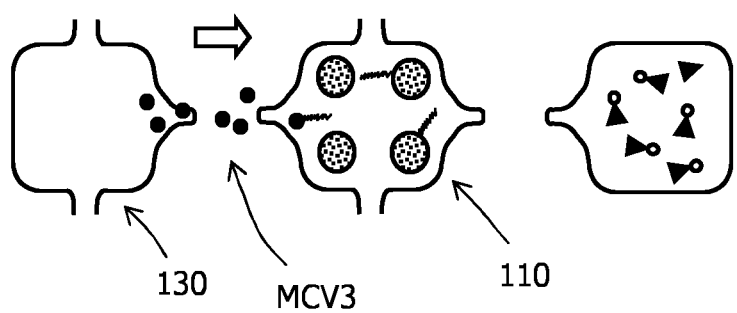
FIG. 4 illustrates the transfer of detection particles into the purification chamber in the system of FIG. 1.

FIG. 4 illustrates the final step of the assay in which magnetic detection particles DP are transferred through the other magneto-capillary valve MCV3 into the purification chamber 110 where they may bind to target components TC. The magnetic detection particles with bound target components are then further bound at the binding spots BS in the purification chamber 110. This binding can in turn be detected with appropriate surface specific detection procedures (not shown) such as Frustrated Total Internal Reflection.

Figure 5:
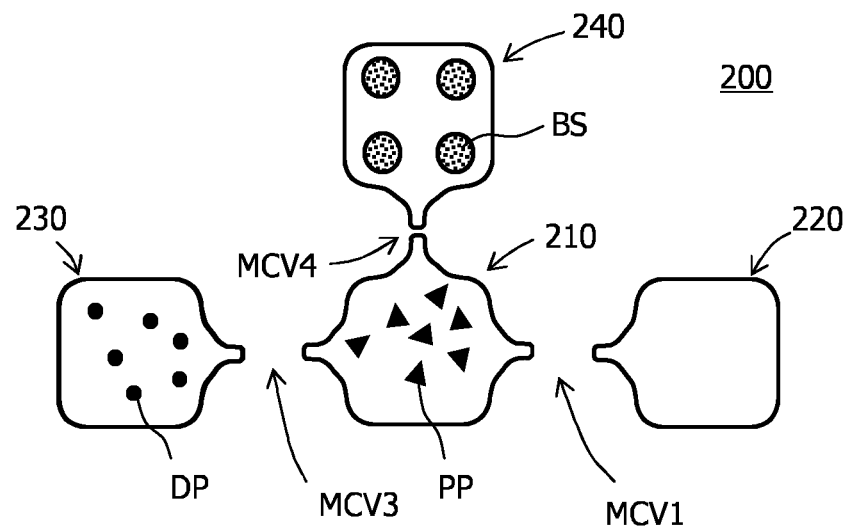
FIG. 5 schematically illustrates another embodiment of a biosensor system that additionally comprises a detection chamber.

FIG. 5 shows a top view onto a second embodiment of a biosensor system 200 in a first stage of a detection assay. As in the first embodiment, the biosensor system 200 comprises a purification chamber 210 in which magnetic purification particles PP are provided and which is connected to a waste chamber 220 via a magneto-capillary valve MCV1, and a detection-particle storage chamber 230 that is connected to the purification chamber 210 via another magneto-capillary valve MCV3. The inlets and outlets of the chambers are not shown in detail for purposes of simplification.

In contrast to the first embodiment, an additional detection chamber 240 is provided that is coupled to the purification chamber 210 via a further magneto-capillary valve MCV4. Now the detection chamber 240 comprises the binding spots BS.

The next steps of the assay are similar to those illustrated in FIGS. 2-4: Introduction of the sample into the purification chamber 210, transfer of purification particles PP with bound interfering components IC into the waste chamber 220, addition of detection particles DP from the respective storage chamber 230 into the purification chamber.

Figure 6:
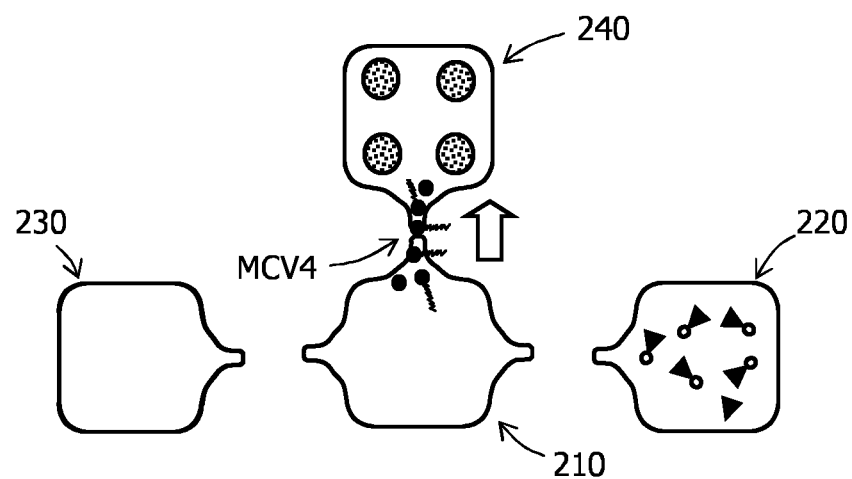
FIG. 6 illustrates the transfer of detection particles with bound target components into the detection chamber in the system of FIG. 5.

The final step of the assay, illustrated in FIG. 6, is however different in that magnetic detection particles DP with or without bound target components TC are magnetically transferred via the further magneto-capillary valve MCV4 into the detection chamber 240. There a clean matrix such as a buffer can be provided (e.g. by punching an integrated pouch), and detection particles DP with bound target components TC can bind to the binding spots.

Figure 7:
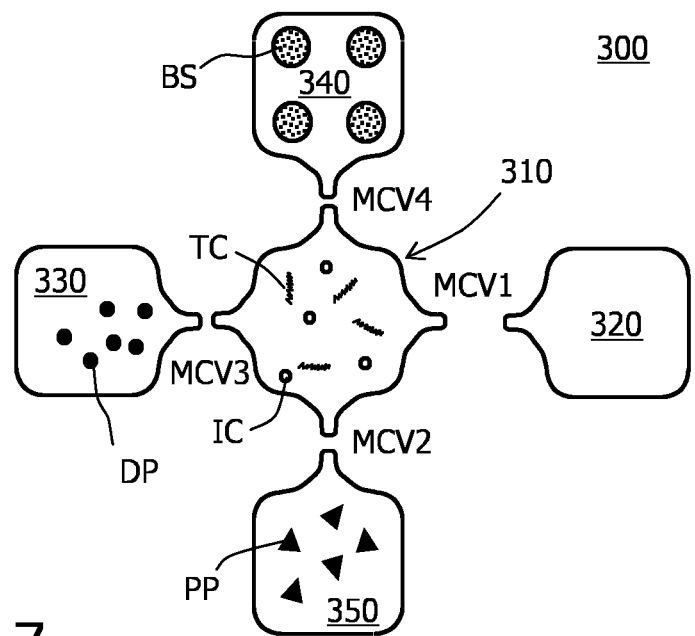
FIG. 7 schematically illustrates another embodiment of a biosensor system that additionally comprises a detection chamber and a purification-particle storage chamber.

FIG. 7 schematically illustrates a third embodiment of a biosensor system 300. As the second biosensor 200, this third system comprises a purification chamber 310, a waste chamber 320 that is connected to the purification chamber via a first magneto-capillary valve MCV1, a detection-particle storage chamber 330 that is connected to the purification chamber via another magneto-capillary valve MCV3, and a detection chamber 340 that is connected to the purification chamber via a further magneto-capillary valve MCV4.

Additionally, a "purification-particle storage chamber" 350 is provided and coupled to the purification chamber 310 via an additional magneto-capillary valve MCV2. During a typical assay in this biosensor system, the following steps are executed:

1. Introduction of a sample to be analyzed into the purification chamber 310.
2. Transfer of purification particles PP from their storage chamber 350 into the purification chamber 310 via the associated magneto-capillary valve MCV2.
3. Transfer of purification particles PP (with or without bound interfering components IC) from the purification chamber 310 via the associated magneto-capillary valve MCV1 into the waste chamber 320.
4. Transfer of detection particles DP from their storage chamber 330 into the purification chamber 310 via the associated magneto-capillary valve MCV3.
5. Transfer of detection particles DP (with or without bound target components TC) from the purification chamber 310 via the associated magneto-capillary valve MCV4 into the detection chamber 340.
6. Binding of magnetic detection particles DP with bound target components TC to the binding spots BS in the detection chamber 340 and detection of these bound particles/components.

Figure 8:
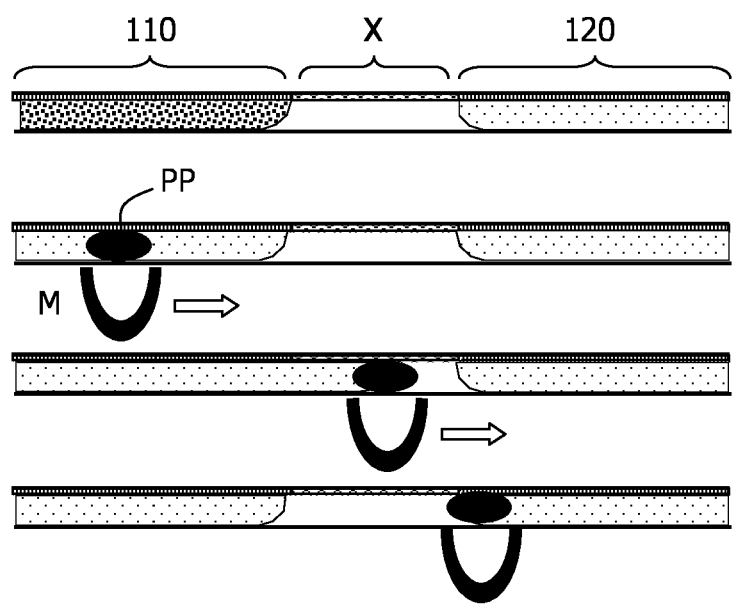
FIG. 8 schematically illustrates the transfer of magnetic particles across a magneto-capillary valve.

The described embodiments of the biosensor systems have been implemented by making use of a micro-capillary valve (MCV). A schematic illustration of the MCV technology is shown in FIG. 8. Here magnetic beads, for example magnetic purification particles PP, can be moved from one fluidic chamber (e.g. the purification chamber 110) to a next fluidic chamber (e.g. the waste chamber 120) over a hydrophobic barrier X with the help of an actively moved magnet M. In general, MCV is about magnetically transferring components bonded to magnetic beads, from one chamber to another chamber through a hydrophobic valve. More details about this technique are disclosed for instance in WO2009083862, WO2010041174, WO2010070461, WO2010140128, WO2011007310 or WO2011042828.

In summary, embodiments of a biosensor system for the detection of target molecules have been described that implement at least some of the following steps:

(1) Providing a 1st chamber with a sample having interfering components and a 2nd chamber, separated from each other by a 1st MCV.
(2) Providing in the 1st chamber magnetic beads/particles arranged to capture interfering components in the sample.
(3) Magnetically transferring the 1st magnetic particles (bonded or not to the interfering components) from the 1st chamber to the 2nd chamber.
(4) Providing 2nd magnetic particles functionalized to capture the target components in the 1st chamber.

Optionally one or more of the following features may additionally be realized:

The 2nd magnetic beads may be stored in a 3rd chamber and be provided through a 2nd MCV separating the 1st and the 3rd chambers.

The biosensor further comprises binding spots functionalized to capture target components or 2nd magnetic beads and provided on a surface of the 1st chamber OR on the surface of a further chamber separated from the 1st chamber by a further MCV.

The described embodiments can be modified and extended in various ways. For example, instead of magnetic purification particles PP, other particles that can controllably be manipulated/moved, e.g. by electrical, acoustic, thermal and/or optical forces or means, can be used as purification particles, too.

Additionally or alternatively, the valves that connect different compartments need not be magneto-capillary valves, particularly if non-magnetic purification particles shall be moved through these valves.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A biosensor system for detection of target components in a sample that comprises interfering components which may interfere with the detection of the target components, comprising:
    a purification chamber with an inlet for introduction of the sample;
    purification particles that can bind interfering components of the sample in the purification chamber;
    a detection-particle storage chamber configured to provide magnetic detection particles, the detection-particle storage chamber comprising a first protrusion that points to a first mirror symmetric protrusion of the purification chamber, wherein the magnetic detection particles bind target components of the sample; wherein the detection particle storage chamber that is connected to the purification chamber via a magneto-capillary valve through which the detection-particles can controllably be moved; and
    a waste chamber that is connected to the purification chamber via a magneto-capillary valve through which the purification particles can controllably be moved, wherein the waste chamber comprises a second protrusion that points toward a second mirror symmetric protrusion of the purification chamber.

2. The biosensor system according to claim 1, wherein the purification particles are adapted to bind interfering components and/or fractions and/or aggregates chosen from the group consisting essentially of: proteins; antibodies; lipids; nucleic acids; cells; bacteria; enzymes; molecules with a certain resemblance to target analytes that may cross-react; and drugs.

3. The biosensor system according to claim 1, wherein the purification particles comprise surface molecules or atoms and/or fractions and/or aggregates are chosen from the group consisting essentially of: proteins; streptavidin; antibodies; nucleic acids; enzymes; electrically charged molecules or atoms; silica molecules; metal atoms; molecules that may react with interfering components such that their degree of interference is decreased; molecules with a resemblance to target analytes; and capture molecules with an affinity for interfering components.

4. The biosensor system according to claim 1, wherein the magnetic detection particles are provided in the purification chamber and/or in a detection-particle storage chamber prior to the introduction of the sample into the purification chamber.

5. The biosensor system according to claim 4, wherein the detection-particle storage chamber is coupled to the purification chamber via another magneto-capillary valve.

6. The biosensor system according to claim 1, wherein the purification particles are moved by magnetic effect.

7. The biosensor system according to claim 1, wherein the purification particles comprise magnetic particles.

8. The biosensor system according to claim 1, wherein at least one binding spot is provided on a surface of the purification chamber and/or of a separate detection chamber for detection of magnetic detection particles with bound target components.

9. The biosensor system according to claim 1, it further comprises a detection chamber that is coupled to the purification chamber by a magneto-capillary valve allowing for transfer of the magnetic detection particles from the purification chamber to the detection chamber.

10. A method for detection of target components in a sample that comprises interfering components which may interfere with the detection of the target components, the method comprising:
    providing the biosensor system of claim 1;
    adding purification particles that can bind interfering components of the sample;
    transferring said purification particles from a purification chamber through the magneto-capillary valve into a waste chamber;

transferring magnetic detection particles that can bind target components to the sample through the magneto-capillary valve into the purification chamber; and detecting said magnetic detection particles with bound target components.

11. The method according to claim 10, wherein the purification particles are added to the sample prior to its introduction into the purification chamber.

12. The method of claim 10, wherein the purification particles are provided in the purification chamber and/or in a purification-particle storage chamber prior to introduction of the sample into the purification chamber.

13. The method according to claim 12, wherein the purification-particle storage chamber is coupled to the purification chamber via a valve, preferably via a magneto-capillary valve.

14. The method according to claim 10, wherein the magnetic detection particles are added to the sample prior to its introduction into the purification chamber.

* * * * *